(12) United States Patent
Henrich et al.

(10) Patent No.: US 8,729,053 B2
(45) Date of Patent: May 20, 2014

(54) NUCLEAR FACTOR KAPPA B PATHWAY INHIBITOR COMPOSITION AND USE OF SAME

(75) Inventors: Curtis J. Henrich, Rockville, MD (US); Moon-II Kang, Gyeongsangnam-do (KR); Heidi R. Bokesch, Frederick, MD (US); Kirk R. Gustafson, Frederick, MD (US); Nancy H. Colburn, Middletown, MD (US); Matthew R. Young, Ijamsville, MD (US); James B. McMahon, Frederick, MD (US)

(73) Assignee: The United States of America, as represented by the Secretary of the Department of Health and Human Services, Washington, DC (US)

( * ) Notice: Subject to any disclaimer, the term of this patent is extended or adjusted under 35 U.S.C. 154(b) by 335 days.

(21) Appl. No.: 13/120,044

(22) PCT Filed: Sep. 22, 2009

(86) PCT No.: PCT/US2009/057761
§ 371 (c)(1),
(2), (4) Date: Apr. 18, 2011

(87) PCT Pub. No.: WO2010/033958
PCT Pub. Date: Mar. 25, 2010

(65) Prior Publication Data
US 2011/0190240 A1    Aug. 4, 2011

Related U.S. Application Data

(60) Provisional application No. 61/098,977, filed on Sep. 22, 2008.

(51) Int. Cl.
| *A01N 33/26* | (2006.01) |
| *A61K 31/655* | (2006.01) |
| *C07C 309/66* | (2006.01) |
| *C07C 317/32* | (2006.01) |
| *A61K 31/10* | (2006.01) |

(52) U.S. Cl.
CPC ............. *C07C 309/66* (2013.01); *C07C 317/32* (2013.01); *A61K 31/10* (2013.01)
USPC ....................................................... 514/150

(58) Field of Classification Search
CPC .................................................. Y10S 514/908
USPC ....................................................... 514/150
See application file for complete search history.

(56) References Cited

U.S. PATENT DOCUMENTS

| 2,784,204 A | 3/1957 | Heyna et al. |
| 3,832,253 A | 8/1974 | Di Palma et al. |
| 3,854,480 A | 12/1974 | Zaffaroni |
| 4,118,381 A | 10/1978 | Fuchs et al. |
| 4,235,871 A | 11/1980 | Papahadjopoulos et al. |
| 4,452,775 A | 6/1984 | Kent |
| 4,501,728 A | 2/1985 | Geho et al. |
| 4,667,014 A | 5/1987 | Nestor, Jr. et al. |
| 4,748,034 A | 5/1988 | de Rham |
| 4,837,028 A | 6/1989 | Allen |
| 5,019,369 A | 5/1991 | Presant et al. |
| 5,075,109 A | 12/1991 | Tice et al. |
| 5,239,660 A | 8/1993 | Ooi |
| 5,502,174 A | 3/1996 | Ehrenberg et al. |
| 5,964,900 A | 10/1999 | Ruhlmann et al. |
| 5,969,114 A | 10/1999 | Wight et al. |
| 5,976,197 A | 11/1999 | Hutchings et al. |

FOREIGN PATENT DOCUMENTS

| EP | 1 134 260 A1 | 9/2001 |
| GB | 2 301 118 | 11/1996 |
| WO | WO 96/35012 A1 | 11/1996 |
| WO | WO 2007/039573 A2 | 4/2007 |

OTHER PUBLICATIONS

Cooper at al., "Expression of Dominant Negative *c-jun* Inhibits Ultraviolet B-Induced Squamous Cell Carcinoma Number and Size in an SKH-1 Hairless Mouse Model," *Mol. Carcinog. Res.*, 1, 848-854 (2003).

Dhar et al., "Dominant-negative c-Jun (TAM67) target genes: HMGA1 is required for tumor promoter-induced transformation," *Oncogene*, 23, 4466-4476 (2004).

(Continued)

*Primary Examiner* — Samira Jean-Louis
(74) *Attorney, Agent, or Firm* — Leydig, Voit & Mayer, Ltd.

(57) ABSTRACT

An embodiment of the invention provides a pharmaceutical composition comprising a compound of formula (I) a pharmaceutically acceptable salt, prodrug, hydrate, or solvate thereof. Another embodiment of the invention provides a method of treating or preventing a condition associated with increased expression and/or activity of an NFκB pathway using same compounds. A further embodiment of the invention provides a method of diagnosing a condition in an individual using same compounds.

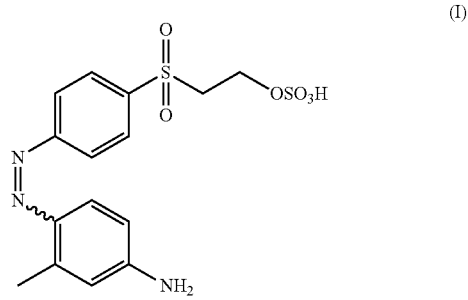

(I)

20 Claims, 10 Drawing Sheets

(56) References Cited

OTHER PUBLICATIONS

Ding et al., "Effects of Polycyclic Aromatic Hydrocarbons (PAHs) on Vascular Endothelial Growth Factor Induction through Phosphatidylinositol 3-Kinase/AP-1-dependent, HIF-1α-independent Pathway," *J. Biol. Chem.*, 281 (14), 9093-9100 (2006).

Dong et al., "A Dominant Negative Mutant of jun Blocking 12-*O*Tetradecanoylphorbol-13-acetate—Induced Invasion in Mouse Keratinocytes," *Mol. Carcinog.*, 19, 204-212 (1997).

Dong et al., "Blocking of tumor promoter-induced AP-1 activity inhibits induced transformation in JB6 mouse epidermal cells," *Proc. Natl. Acad. Sci., USA*, 91, 609-613 (1994).

Greten et al., "The IKK/NF-κB activation pathway—a target for prevention and treatment of cancer," *Cancer Lett.*, 206, 193-199 (2004).

International Preliminary Report on Patentability, Application No. PCT/US2009/057761, dated Mar. 22, 2011.

International Search Report, Application No. PCT/US2009/057761, dated Nov. 26, 2009.

Karin et al., "NF-κB in Cancer: From Innocent Bystander to Major Culprit," *Nat. Rev. Cancer*, 2, 301-310 (2002).

Kim et al., "Transcriptional Regulation of Cyclooxygenase-2 in Mouse Skin Carcinoma Cells," *J. Biol. Chem.*, 273 (42), 27686-27694 (1998).

Lee et al., "Dyeing of wool with temporarily solubilised disperse dyes," *Color. Technol.*, 117 (4), 212-216 (2001).

Lee et al., "Synthesis of Temporarily Solubilized Reactive Disperse Dyes and Their Application to the Polyester/Cotton Blend Fabric," *Fibers and Polymers*, 3 (3), 85-90 (2002).

Li et al., "Induced Expression of Dominant-Negative *c-jun* Downregulates NFκB and AP-1 Target Genes and Suppresses Tumor Phenotype in Human Keratinocytes," *Mol. Carcinog.*, 29, 159-169 (2000).

Li et al., "Expression of dominant negative Jun inhibits elevated AP-1 and NF-κB transactivation and suppresses anchorage independent growth of HPV immortalized human keratinocytes," *Oncogene*, 16, 2711-2721 (1998).

Matthews et al., "Dominant-Negative Activator Protein 1 (TAM67) Targets Cyclooxygenase-2 and Osteopontin under Conditions in which It Specifically Inhibits Tumorigenesis," *Cancer Res.*, 67 (6), 2430-2438 (2007).

Ruocco et al., "A High-Throughput Cell-Based Assay to Identify Specific Inhibitors of Transcription Factor AP-1," *J. Biomol. Screen.*, 12, 133-139 (2007).

Shaulian et al., "AP-1 as a regulator of cell life and death," *Nat. Cell. Biol.*, 4 (5), E131-E136 (2002).

Shen et al., "Targeting the Activator Protein 1 Transcription Factor for the Prevention of Estrogen Receptor—Negative Mammary Tumors," *Cancer Prev. Res.*, 1 (1), 45-55 (2008).

Silberman et al., "Characterization of Downstream Ras Signals That Induce Alternative Protease-dependent Invasive Phenotypes," *J. Biol. Chem.*, 272 (9), 5927-5935 (1997).

Suzukawa et al., "AP-1, NFκB, and ERK Activation Thresholds for Promotion of Neoplastic Transformation in the Mouse Epidermal JB6 Model," *Environ. Health Perspect.*, 110, 865-870 (2002).

Szoka et al., "Comparative Properties and Methods of Preparation of Lipid Vesicles (Liposomes)," *Annu. Rev. Biophys. Bioeng.*, 9, 467-508 (1980).

Thompson et al., "A Dominant Negative c-jun Specifically Blocks Okadaic Acid-induced Skin Tumor Promotion," *Cancer Res.*, 62, 3044-3047 (2002).

Uwe et al., "Anti-inflammatory interventions of NF-κB signaling: Potential applications and risks," *Biochem. Pharmacol.*, 75, 1567-1579 (2008).

Wang et al., "Identification of a novel nuclear factor-kappaB sequence involved in expression of urokinase-type plasminogen activator receptor," *Eur. J. Biochem.*, 267, 3248-3254 (2000).

Wang of al., "Molecular Cloning, Characterisation and Ligand-bound Structure of an Azoreductase from *Pseudomonas aeruginosa*," *J. Mol. Biol.*, 373 (5), 1213-1228 (2007).

Young et al., "Protection Against Human Papillomavirus Type 16-E7 Oncogene-Induced Tumorigenesis by In Vivo Expression of Dominant-Negative c-*jun*," *Mol. Carcinog.*, 34, 72-77 (2002).

Young et al., "Transgenic mice demonstrate AP-1 (activator protein-1) transactivation is required for tumor promotion," *Proc. Natl. Acad. Sci, USA*, 96, 9827-9832 (1999).

Young et al., "Promising molecular targets for cancer prevention: AP-1, NF-κB and Pdcd4," *Trends Mol. Med.*, 9 (1), 36-41 (2003).

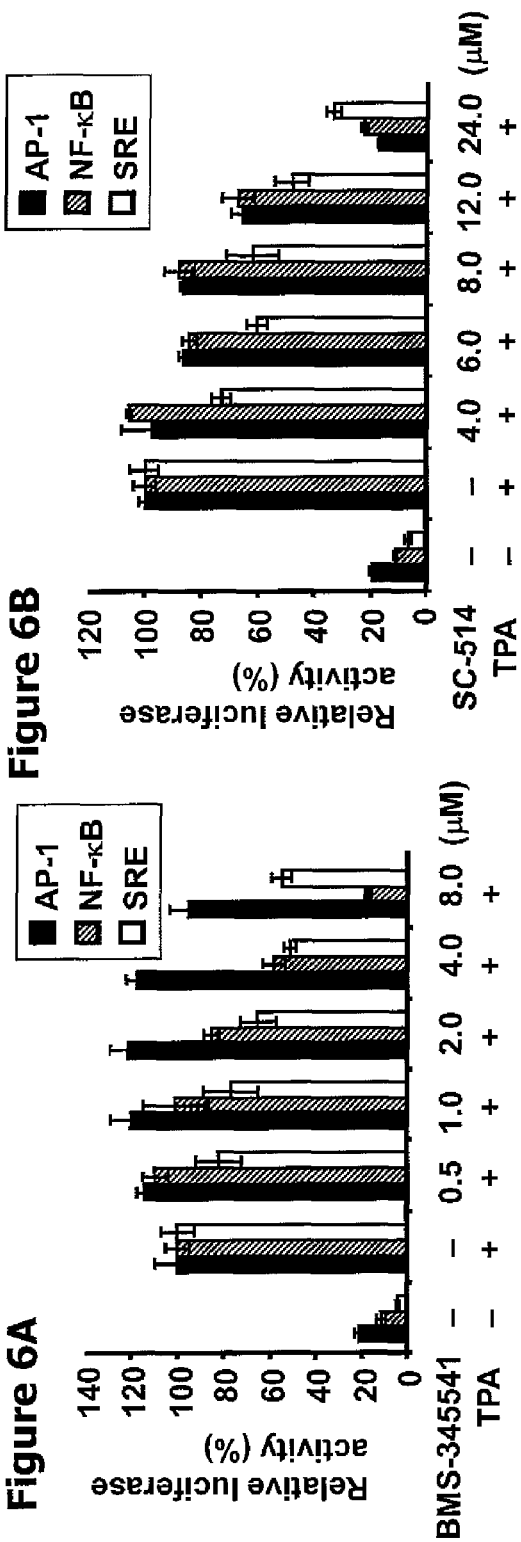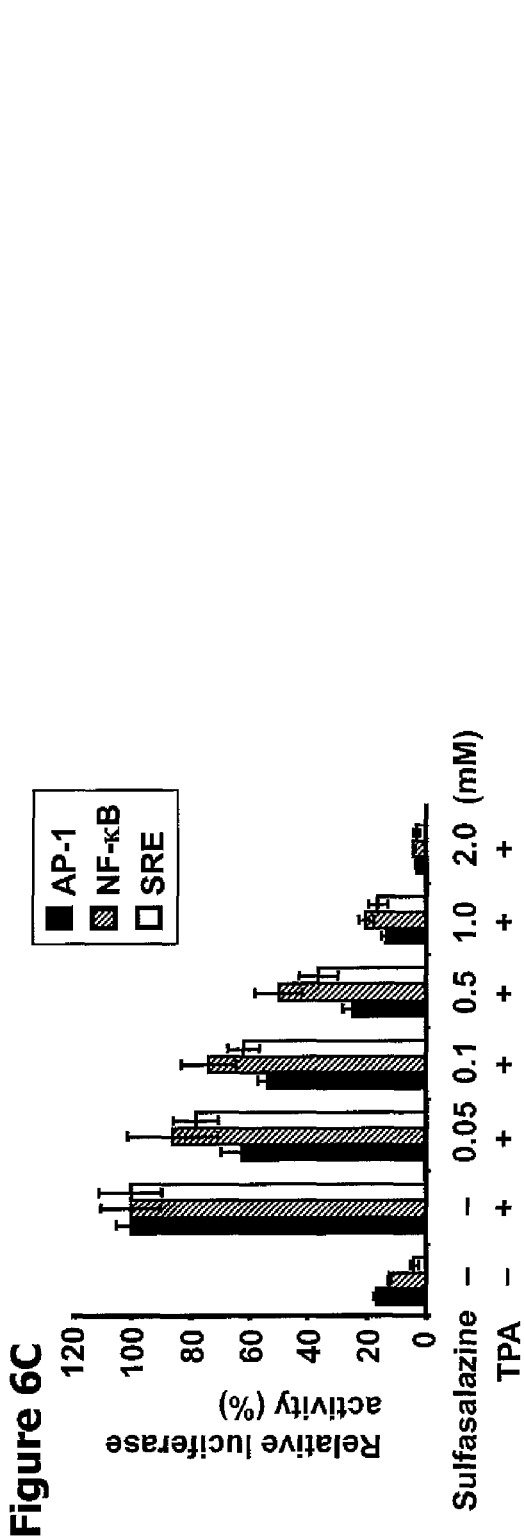

NUCLEAR FACTOR KAPPA B PATHWAY INHIBITOR COMPOSITION AND USE OF SAME

CROSS-REFERENCE TO RELATED APPLICATIONS

This patent application is a U.S. National Phase of International Patent Application No. PCT/US09/57761, filed Sep. 22, 2009, which claims the benefit of U.S. Provisional Patent Application No. 61/098,977, filed Sep. 22, 2008, which are incorporated by reference.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 2,433 Byte ASCII (Text) file named "707794ST25.TXT," created on Mar. 1, 2011.

BACKGROUND OF THE INVENTION

The nuclear factor kappa B (NFκB) cellular pathways are important for normal cellular function and for regulation of the immune system, such as mediating responses to antigens and cytokines. However, an increase in the expression and/or activity of an NFκB pathway is associated with certain diseases and conditions, such as breast cancer and inflammation. Therefore, there is a desire to provide compositions and methods to inhibit NFκB pathways.

BRIEF SUMMARY OF THE INVENTION

The invention, in an embodiment, provides a pharmaceutical composition comprising (i) compound I

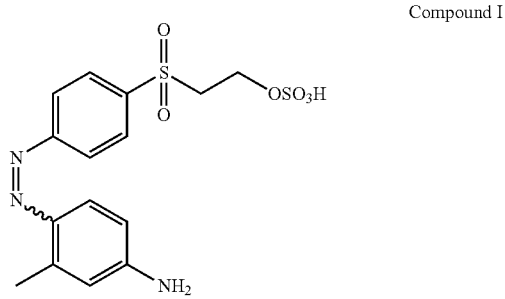

Compound I a pharmaceutically acceptable salt, prodrug, hydrate, or solvate thereof, and (ii) a pharmaceutically acceptable carrier.

The invention also provides a method of treating or preventing a condition associated with increased expression and/or activity of an NFκB pathway, the method comprising administering to an individual in need thereof an effective amount of compound I, a pharmaceutically acceptable salt, prodrug, hydrate, or solvate thereof.

In a further embodiment, the invention provides a method of diagnosing a condition in an individual, wherein said condition is suspected to be associated with an increased expression and/or activity of an NFκB pathway, the method comprising (i) contacting a sample from the individual with compound I, a pharmaceutically acceptable salt, prodrug, hydrate, or solvate thereof, (ii) measuring the expression and/or activity of an NFκB pathway in the sample, and (iii) comparing the expression and/or activity measured in (ii) with that of a sample exhibiting the condition not in the presence of the compound, pharmaceutically acceptable salt, prodrug, hydrate, or solvate thereof; whereby a decrease in the expression and/or activity in the contacted sample indicates that the individual has a condition associated with increased expression and/or activity of an NFκB pathway.

BRIEF DESCRIPTION OF THE DRAWINGS

FIG. 6A is a bar graph showing relative luciferase reporter activity of AP-1, NFκB, and SRE promoters in the presence of BMS-345541 and in the presence or absence of TPA.

FIG. 6B is a bar graph showing relative luciferase reporter activity of AP-1, NFκB, and SRE promoters in the presence of SC-514 and in the presence or absence of TPA.

FIG. 6C is a bar graph showing relative luciferase reporter activity of AP-1, NFκB, and SRE promoters in the presence of sulfasalazine and in the presence or absence of TPA.

DETAILED DESCRIPTION OF THE INVENTION

Figure 1A:
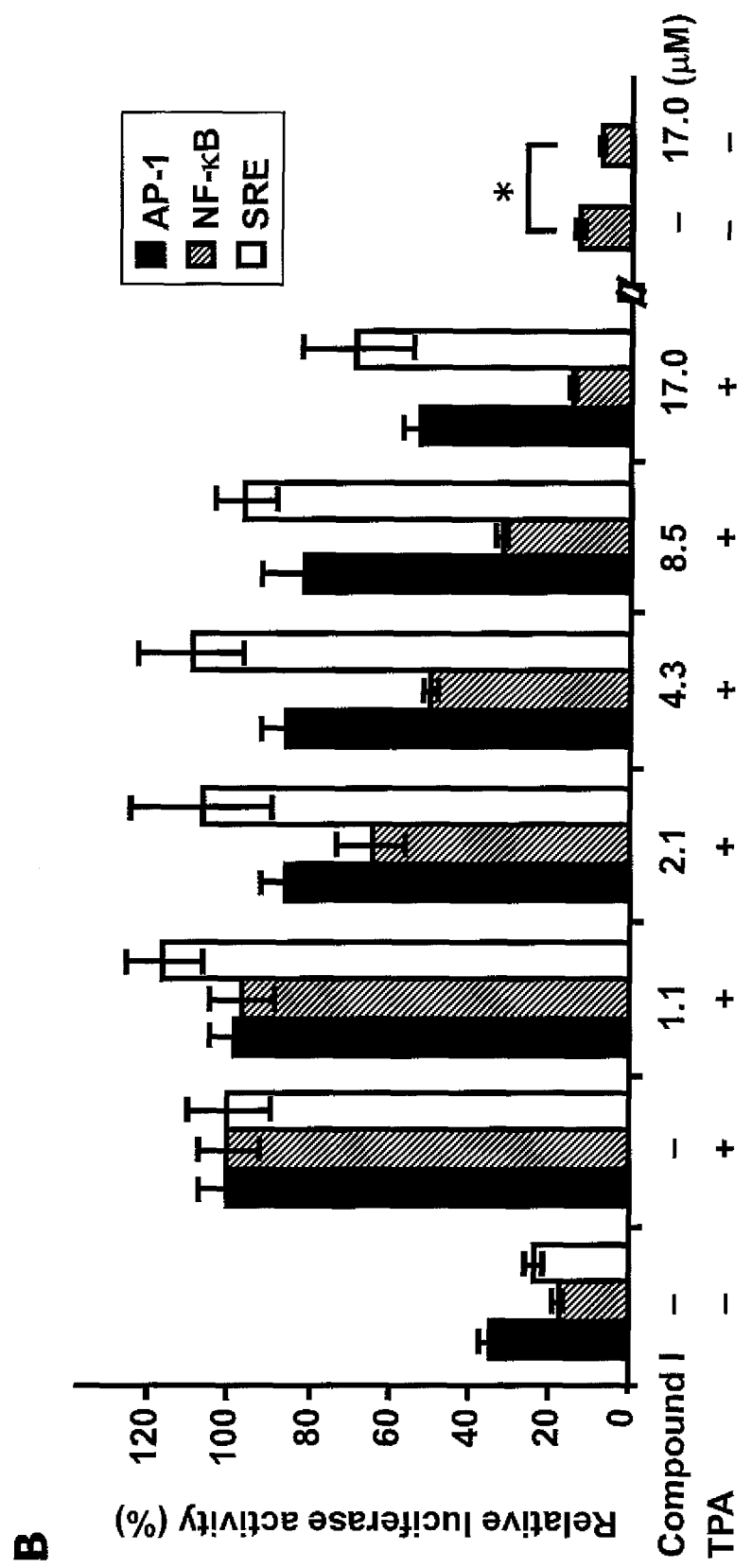
FIG. 1A is a bar graph showing relative luciferase reporter activity of AP-1, NFκB, and SRE promoters in the presence of increasing concentrations of compound I.

The invention provides, in accordance with an embodiment, a pharmaceutical composition comprising (i) compound I

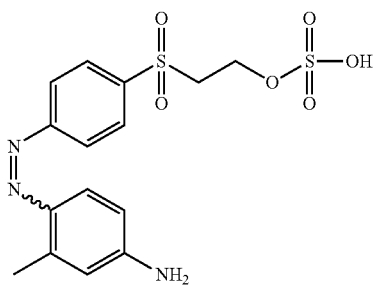

Compound I a pharmaceutically acceptable salt, prodrug, hydrate, or solvate thereof; and (ii) a pharmaceutically acceptable carrier. Compound I may exist in the Z (cis) configuration or the E (trans) configuration, or a mixture of Z and E, which may be enriched in one of the isomers, such as 90/10, 80/20, 70/30, 60/40, or 50/50 with respect to each of Z and E. A prodrug of compound I is a compound which releases compound I in the body. For example, the amino group may be converted to an amide, carbonate, etc., and the sulfate group may be converted to a diester, amide, carbonate, etc. Such prodrugs may be converted in the body, e.g., blood, or hydrolyzed, for example, in the acidic or alkaline conditions of the gastroenteric system. Compound I may be covalently attached to, for example, polyethylene glycol and/or saccharides (such as mono- and/or polysaccharides) using these linkages. For additional information on prodrugs, see Higuchi and Stella, Prodrugs as Novel Delivery Systems, 14 of the ACS Symposium Series, 14, 1975; Bundgaard, H., "Design of Bioreversible Drug Derivatives and the Utility of the Double Prodrug Concept" In Bioreversible Carriers in Drug Design; Roche, E. B., Ed.; Pergamon Press: New York, 1987, which are incorporated by reference.

A hydrate of compound I is compound I associated with a water molecule or molecules, such as 0.5, 1, 1.5, 2, 2.5, 3, or more water molecules per molecule of compound I. Such association may occur in the solid state upon crystallization of compound I or upon lyophilization of compound I.

A solvate of compound I is compound I associated with a solvent molecule. For example, compound I may be dissolved in a solvent such as methanol, ethanol, acetone, acetonitrile, etc. Upon drying, the solid form of the compound may continue to be associated with molecules of the solvent.

The invention provides, in another embodiment, a method of treating or preventing a condition associated with increased expression and/or activity of an NFκB pathway, the method comprising administering to an individual in need thereof an effective amount of compound I, a pharmaceutically acceptable salt, prodrug, hydrate, or solvate thereof.

In a further embodiment, the invention provides a method of diagnosing a condition in an individual, wherein said condition is suspected to be associated with an increased expression and/or activity of an NFκB pathway, the method comprising (i) contacting a sample from the individual with compound I, a pharmaceutically acceptable salt, prodrug, hydrate, or solvate thereof, (ii) measuring the expression and/or activity of an NFκB pathway in the sample, and (iii) comparing the expression and/or activity measured in (ii) with that of a sample exhibiting the condition not in the presence of the compound, pharmaceutically acceptable salt, prodrug, hydrate, or solvate thereof, whereby a decrease in the expression and/or activity in the contacted sample indicates that the individual has a condition associated with increased expression and/or activity of an NFκB pathway.

Preferably, the individual is a mammal. The mammal can be any suitable mammal, such as a mammal selected from the group consisting of a mouse, rat, guinea pig, hamster, cat, dog, pig, cow, horse, and primate. The mammal preferably is a human, especially a human patient.

NFκB comprises two separate protein complexes. The first complex comprises the proteins p50 and p65 (also known as RelA). p50 is often referred to as NFκB1. The second complex comprises p52 and RelB. p52 is often referred to as NFκB2. These complexes are involved in separate but related NFκB pathways. All of these proteins share homology in their N-terminal domains, named a Rel homology domain. p50 and p52 are products of larger proteins, p105 and p100, respectively, which are processed by the ubiquitin/proteasome pathway.

Transduction of the NFκB pathway signals are initiated through external stimuli of a cell. A ligand, such as cytokines or TNFα, binds to its plasma transmembrane cell receptor, activating the receptor. The signal is then transduced from the receptors through the canonical NFκB pathway (involving NFκB1) and/or the alternative NFκB pathway (involving NFκB2). In the canonical pathway, a complex of IκBα kinase (IKK) proteins, IKKα/β/γ, is activated and phosphorylates the protein IκBα, which is associated with p50 and p65, causing dissociation of IκBα. The IκBα interaction with p50 and p65 is inhibitory, and p50/p65 is then activated through dissociation of IκBα. The p50/p65 complex is imported into the nucleus where it acts as a transcription factor, thus activating gene transcription. In the alternative pathway, the signal from the cell receptor is transmitted through the protein NIK, which activates IKKα. This ultimately activates the p52/RelB complex. The p52/RelB complex is imported into the nucleus where it also acts as a transcription factor and activates gene transcription.

Increased expression and/or activity of an NFκB pathway includes overexpression or hyperactivity of any component of an NFκB pathway.

There are many known inhibitors of NFκB pathways. These include, for example without limitation, ibuprofen, sulindac, curcumin, aspirin, sulfasalazine, SC-514, BMS-345541, MLN120B or PS-1145.

Overexpression and/or hyperactivity of the NFκB pathways is well known to cause many adverse conditions. These include, for example, inflammation, colitis, diabetes, prostatitis, pancreatitis, atherosclerosis, inflammatory bowel disease, rheumatoid arthritis, gastritis, asthma, cancer tumorigenesis, and/or cancer progression.

AP-1 activation is important in regulating genes involved in normal cell proliferation, differentiation, development and responses to external stimuli. NFκB and AP-1 are regulated by different signaling pathways; however, cross-talk between these pathways occurs, mediated in part by the ability of certain of the Jun and Fos family proteins to interact with NFκB p65. Environmentally induced AP-1 dependent transcription can contribute not only to normal physiological processes but also to tumor promotion and progression. AP-1 activity is often elevated in human and mouse cancers (via elevated Ras-MAPK signaling) and this elevation is required both to induce and to maintain tumor phenotype. Tumor promoter induced AP-1 activation can be repressed by a dominant-negative c-Jun, TAM67, in a transgenic mouse model, inhibiting tumorigenesis and tumor progression without inhibiting cell proliferation or cell survival. Compound I was determined to have an $IC_{50}$ value of 17 μM for inhibition of TPA induced AP-1.

The compound I, pharmaceutically acceptable salt, prodrug, hydrate, or solvate thereof of the invention can be prepared by suitable methods as would be known to those skilled in the art or isolated. For example, isolation may be accomplished through isolation of NSC676914 as disclosed in Example 1, below. Additionally, compound I may be prepared through methods disclosed in, e.g., U.S. Pat. No. 5,976,197.

As demonstrated in the Examples, below, with an $IC_{50}$ of about 4 µM for inhibition of NFκB reporter, compound I reduces phosphorylation of IKKα/β significantly. The repressed phosphorylation of IKK produced complete blocking of phosphorylation on IκBα at concentrations as low as 8.5 µM. The phosphorylation of IκBα was reduced even at 1.1 µM compound I compared to its level with TPA induction alone. Concentrations of compound I as low as 1.1 µM repressed NFκB DNA binding and transcriptional activation of NFκB dependent genes. Moreover compound I inhibits tumor promoter induced transformation of JB6 cells and invasion of breast cancer cells.

Compound I was found to inhibit IKKβ without targeting MAP kinases or JAKs that activate STAT3. As a consequence of targeting IKKβ, compound I regulates the canonical pathway of NFκB activation. This results in interception of nuclear translocation of p50/65. Although the expression of cytoplasmic p100 and nuclear p52 was reduced, compound I did not inhibit the processing of p100 to p52 that is known to depend on IKKα. Another IKKβ-dependent event also inhibited by compound I is the phosphorylation of p65 at Ser536. As Ser536 phosphorylation is important in p65 transactivation, this activity may contribute to the observed inhibition of NFκB-Luciferase. The IKKβ pathway of activating NFκB plays a role in innate immune response. NFκB activation is also involved in tumor promotion, progression, and several inflammation-associated diseases. These inflammatory diseases are in some cases regulated by an over-activation of IKKβ.

It is contemplated that compound I acts as an upstream inhibitor of the canonical pathway at a junction where the canonical and alternative pathways diverge. Therefore, compound I may inhibit the alternative and canonical pathways.

The NCI cancer screen data for compound I in the NCI-60 panel of human cancer cell lines showed that leukemia and breast cancer cell lines are more sensitive to compound I for growth inhibition than lines from other cancer sites tested. Compound I at 1 µM inhibits the growth of leukemia lines more than 50% but does not kill these leukemia lines at concentrations up to 100 µM. Most of the NCI-60 human cancer cell lines showed growth inhibition at greater than 10 µM. Thus in addition to inhibiting tumorigenesis (transformation) and tumor progression (invasion), compound I may have potential for tumor growth inhibition in some cancer sites.

NFκB selective inhibitors are important for cancer prevention and treatment. Obligatory relationships between NFκB activation and inflammation-associated cancer have been demonstrated using several mouse models. NFκB activation has been implicated in inflammation associated liver, prostate and colon cancer induction in humans and mouse models. Several antioxidants having electrophilic capacity such as cyclopentenone prostaglandins, dimethoxylsulfoxide, glutathione and non-steroidal anti-inflammatory drugs (NSAIDs) Ibuprofen, sulindac, as well as curcumin inhibit NFκB activity but do not show high selectivity. Aspirin, sulfasalazine, SC-514, and PS-1145 also inhibit NFκB by interrupting phosphorylation of IKK.

Compound I shows no activity to bind to the ATP binding pocket of IKKβ. The ATP-binding domains of protein kinases are very similar across kinases. As a result, inhibitors that bind in this region tend to have effects on multiple kinases. By contrast, inhibitors that act at other sites have higher likelihood of showing specificity to specific individual kinases or very closely related kinases. Also, unlike the NFκB inhibitor MLN120B, compound I does not suppress cell proliferation.

The present invention provides a pharmaceutical composition comprising a pharmaceutically acceptable carrier and compound I, preferably an effective amount, e.g., a therapeutically effective amount, including a prophylactically effective amount, of compound I, pharmaceutically acceptable salt, prodrug, hydrate, or solvate thereof.

The pharmaceutically acceptable carriers described herein, for example, vehicles, adjuvants, excipients, or diluents, are well known to those who are skilled in the art and are readily available to the public. The pharmaceutically acceptable carrier can be any of those conventionally used and is limited only by chemico-physical or biological considerations, such as solubility and lack of reactivity with the compound I, lack of detrimental side effects or toxicity under the conditions of use, and route of administration. The choice of carrier will be determined in part by the particular form of compound I (e.g. any pharmaceutically acceptable salt, prodrug, hydrate, or solvate thereof). It will be appreciated by one of skill in the art that, in addition to the following described pharmaceutical compositions, the compounds of the present invention can be formulated as inclusion complexes, such as cyclodextrin inclusion complexes, or liposomes. Pharmaceutically acceptable carriers include, but are not limited to, USP water, saline, Cremophor EL (Sigma Chemical Co., St. Louis, Mo.), propylene glycol, polyethylene glycol, alcohol, and combinations thereof. There is a wide variety of suitable formulations of the composition. The pharmaceutical compositions may be administered as, for example, oral, aerosol, parenteral, subcutaneous, intravenous, intraarterial, intramuscular, interperitoneal, intrathecal, intratumoral, rectal, and vaginal formulations.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

Suitable carriers and their formulations are further described in A. R. Gennaro, ed., *Remington: The Science and Practice of Pharmacy* (19th ed.), Mack Publishing Company, Easton, Pa. (1995).

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound I, pharmaceutically acceptable salt, prodrug, hydrate, or solvate thereof can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compound I, pharmaceutically acceptable salt, prodrug, hydrate, or solvate thereof may be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

Additionally, the compound I, pharmaceutically acceptable salt, prodrug, hydrate, or solvate thereof may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

The compound I, pharmaceutically acceptable salt, prodrug, hydrate, or solvate thereof or a composition thereof can also be administered as a pharmaceutically acceptable acid-addition, base neutralized or addition salt, formed by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base, such as sodium hydroxide, ammonium hydroxide, potassium hydroxide, and organic bases, such as mono-, di-, trialkyl, and aryl amines and substituted ethanolamines. The conversion to a salt is accomplished by treatment of the base compound with at least a stoichiometric amount of an appropriate acid. Typically, the free base is dissolved in an inert organic solvent such as diethyl ether, ethyl acetate, chloroform, ethanol, methanol, and the like, and the acid is added in a similar solvent. The mixture is maintained at a suitable temperature (e.g., between 0° C. and 50° C.). The resulting salt precipitates spontaneously or can be brought out of solution with a less polar solvent.

Preservatives may be used. Suitable preservatives may include, for example, methylparaben, propylparaben, sodium benzoate, and benzalkonium chloride. A mixture of two or more preservatives optionally may be used. The preservative or mixtures thereof are typically present in an amount of about 0.0001% to about 2% by weight of the total composition.

Suitable buffering agents may include, for example, citric acid, sodium citrate, phosphoric acid, potassium phosphate, and various other acids and salts. A mixture of two or more buffering agents optionally may be used. The buffering agent or mixtures thereof are typically present in an amount of about 0.001% to about 4% by weight of the total composition.

Topically applied compositions are generally in the form of liquids, creams, pastes, lotions and gels. Topical administration includes application to the oral mucosa, which includes the oral cavity, oral epithelium, palate, gingival, and the nasal mucosa. In some embodiments, the composition contains at least one active component and a suitable vehicle or carrier. It may also contain other components, such as an anti-irritant. The carrier can be a liquid, solid or semi-solid. In embodiments, the composition is an aqueous solution. Alternatively, the composition can be a dispersion, emulsion, gel, lotion or cream vehicle for the various components. In one embodiment, the primary vehicle is water or a biocompatible solvent that is substantially neutral or that has been rendered substantially neutral. The liquid vehicle can include other materials, such as buffers, alcohols, glycerin, and mineral oils with various emulsifiers or dispersing agents as known in the art to obtain the desired pH, consistency and viscosity. It is possible that the compositions can be produced as solids, such as powders or granules. The solids can be applied directly or dissolved in water or a biocompatible solvent prior to use to form a solution that is substantially neutral or that has been rendered substantially neutral and that can then be applied to the target site. In embodiments of the invention, the vehicle for topical application to the skin can include water, buffered solutions, various alcohols, glycols such as glycerin, lipid materials such as fatty acids, mineral oils, phosphoglycerides, collagen, gelatin and silicone based materials.

The concentration of compound I, pharmaceutically acceptable salt, prodrug, hydrate, or solvate thereof of the invention in the pharmaceutical formulations can vary, e.g., from less than about 1%, usually at or at least about 10%, to as much as 20% to 50% or more by weight, and can be selected primarily by fluid volumes, and viscosities, in accordance with the particular mode of administration selected.

The terms "treat" and "prevent" as well as words stemming therefrom, as used herein, do not necessarily imply 100% or complete treatment or prevention. For example, it can include 10, 20, 30, 40, 50, 60, 70, 80, or 90%. Rather, there are varying degrees of treatment or prevention of which one of ordinary skill in the art recognizes as having a potential benefit or therapeutic effect. In this respect, the inventive methods can provide any amount of any level of treatment or prevention of a condition associated with, e.g., increased expression and/or activity of NFκB pathways. Furthermore, the treatment or prevention provided by the inventive method can include treatment or prevention of one or more conditions or symptoms of the disease being treated or prevented. Also, for purposes herein, "prevention" can encompass delaying the onset of the disease, or a symptom or condition thereof, and includes, e.g., prevention of conversion of pre-malignant tissues to malignant tissues as well as preventing metastasis.

The term "diagnosing" means to make a determination that an individual has and/or is suffering from a certain condition or disease-state.

A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., breast cancer or leukemia and the biopsy may be performed on breast or blood cells to determine whether the condition or disease is caused by increased expression and/or activity of an NFκB pathway.

An "effective amount" refers to a dose that is adequate to prevent or treat a disease or condition associated with increased expression and/or activity of an NFκB pathway. Amounts effective for a therapeutic or prophylactic use will depend on, for example, the stage and severity of the condition, disease or disorder being treated, the age, weight, and general state of health of the patient, and the judgment of the prescribing physician. The size of the dose will also be determined by the compound selected, method of administration, timing and frequency of administration as well as the existence, nature, and extent of any adverse side-effects that might accompany the administration of a particular compound and the desired physiological effect. It will be appreciated by one of skill in the art that various conditions, diseases or disorders could require prolonged treatment involving multiple administrations, perhaps using compound I, a pharmaceutically acceptable salt, prodrug, hydrate, or solvate thereof in each or various rounds of administration. Typical doses might be, for example, 0.1 mg to 1 g daily, such as 5 mg to 500 mg daily. In an embodiment, where the compound is used for preventing a condition, the dose administered may be smaller than for therapeutic use. Thus, the compound may be administered in an amount that might be, for example, 0.01 mg to 250 mg daily, such as 0.05 mg to 100 mg daily.

Methods for preparing administrable (e.g., parenterally administrable) compositions are known or apparent to those skilled in the art and are described in more detail in, for example, Remington's Pharmaceutical Science (17th ed., Mack Publishing Company, Easton, Pa., 1985).

In addition to the aforedescribed pharmaceutical compositions, compound I, a pharmaceutically acceptable salt, prodrug, hydrate, or solvate thereof can be formulated as inclusion complexes, such as cyclodextrin inclusion complexes, or liposomes. Liposomes can serve to target compound I, a pharmaceutically acceptable salt, prodrug, hydrate, or solvate thereof to a particular tissue. Liposomes also can be used to increase the half-life of compound I, a pharmaceutically acceptable salt, prodrug, hydrate, or solvate thereof. Many methods are available for preparing liposomes, as described in, for example, Szoka et al., Ann. Rev. Biophys. Bioeng., 9, 467 (1980) and U.S. Pat. Nos. 4,235,871, 4,501,728, 4,837,028, and 5,019,369.

The delivery systems useful in the context of embodiments of the invention may include time-released, delayed release, and sustained release delivery systems such that the delivery of the inventive composition occurs prior to, and with sufficient time to cause, sensitization of the site to be treated. The inventive composition can be used in conjunction with other therapeutic agents or therapies. Such systems can avoid repeated administrations of the inventive composition, thereby increasing convenience to the subject and the physician, and may be particularly suitable for certain composition embodiments of the invention.

Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775, 4,667,014, 4,748,034, and 5,239,660 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

When compound I, a pharmaceutically acceptable salt, prodrug, hydrate, or solvate thereof is administered with one or more additional therapeutic agents, one or more additional therapeutic agents can be coadministered to the mammal. By "coadministering" is meant administering one or more additional therapeutic agents and compound I, a pharmaceutically acceptable salt, prodrug, hydrate, or solvate thereof sufficiently close in time such that compound I, a pharmaceutically acceptable salt, prodrug, hydrate, or solvate thereof can enhance the effect of one or more additional therapeutic agents. In this regard, compound I, a pharmaceutically acceptable salt, prodrug, hydrate, or solvate thereof can be administered first and the one or more additional therapeutic agents can be administered second, or vice versa. Alternatively, compound I, a pharmaceutically acceptable salt, prodrug, hydrate, or solvate thereof and the one or more additional therapeutic agents can be administered simultaneously.

The present invention further provides a use of a compound or salt in the manufacture of a medicament for treating or preventing a condition associated with increased expression and/or activity of an NFκB pathway. In certain embodiments, the condition is cancer tumorigenesis or tumor progression. In certain preferred embodiments, the cancer is in an epithelial tissue, the cancer is breast cancer, or the cancer is leukemia. In certain embodiments, the condition is inflammation. In certain preferred embodiments, the condition is colitis, diabetes, prostatitis, pancreatitis, atherosclerosis, inflammatory bowel disease, rheumatoid arthritis, gastritis, or asthma. The medicament typically is a pharmaceutical composition as described herein. The medicament can include one or more additional compounds that inhibit the NFκB pathway, for example, ibuprofen, sulindac, curcumin, aspirin, sulfasalazine, SC-514, BMS-345541, MLN120B or PS-1145.

The following examples further illustrate the invention but, of course, should not be construed as in any way limiting its scope.

EXAMPLE 1

This example illustrates a method of isolating and identifying compound I in accordance with an embodiment of the invention.

Compound I was isolated from NSC 676914, provided by the Drug Synthesis and Chemistry Branch, Developmental Therapeutics Program, Division of Cancer Treatment and Diagnosis, National Cancer Institute (Frederick, Md.). Compound I was isolated by HPLC on Rainin Dynamax C18 (2×25 cm) reversed-phase HPLC eluting with a gradient of 20-60% acetonitrile in 0.05% aqueous TFA in 40 min at a flow rate of 10 ml/min to provide compound I: 2-(4-((4-amino-4-methylphenyl)diazenyl)phenylsulfonyl)ethyl hydrogen sulfate. The structure of compound I was assigned based on spectroscopic characterization and comparison to literature data of structurally related compounds. $^1$H NMR (DMSO, 500 MHz) δ 7.97 (2H, d, J=7.5 Hz, H-2' and H-6'), 7.87 (2H, d, J=8.0 Hz, H-3' and H-5'), 7.61 (1H, d, J=9.0 Hz, H-5), 6.52 (1H, s, H-3), 6.48 (1H, d, J=7.5 Hz, H-6), 3.96 (2H, d, J=6.5 Hz, H-8'), 3.65 (2H, d, J=6.5 Hz, H-7'), 2.55 (3H, s, H-7)). $^{13}$C NMR (DMSO, 125 MHz) δ 155.98 (C-1'), 154.21 (C-4), 142.82 (C-1), 141.10 (C-2), 138.32 (C-4'), 129.18 (C-2' and C-6'), 122.18 (C-3' and H-5'), 117.49 (C-6), 113.99 (C-3), 112.34 (C-5), 59.25 (C-8'). 54.87 (C-7'), 20.67 (C-7).

EXAMPLE 2

This example illustrates how NFκB activation and inhibition were measured.

Transfection and Luciferase Reporter Assay

All expression plasmids were transiently transfected into HEK293 cells in a 96-well plate (0.1 μg/well) by using Effectene transfection reagent (Qiagen, Valencia, Calif.) according to the manufacturer's manual. HEK293 cells were maintained in Dulbecco's modified Eagle medium (Sigma, St. Louis, Mo.) supplemented with 10% fetal bovine serum (Atlanta Biologicals, Lawrenceville, Ga.) and incubated at 37° C. in a 5% $CO_2$ incubator. After 24 hrs incubation, the medium was changed to DMEM with 0.2% FBS, and the transfectants were exposed to various concentrations of compound I and TPA (10 ng/ml). Cells were lysed with passive lysis buffer and the luciferase assay was performed using the Firefly-Luciferase reporter assay system (Promega, Madison, Wis.) and MLX Luminometer (Dynex Technology, Chantilly, Va.).

Plasmids

Three different luciferase reporter genes, AP-1 reporter containing four times TRE consensus originated from GCN4 and SRE reporter purchased from Stratagene (La Jolla, Calif.) respectively are as described previously (Suzukawa et al., Environ. Health Perspect., 2002, 110, 865-70). NFκB reporter is driven by five times NFκB responsive element inserted into Cis-reporter backbone (Stratagene, La Jolla, Calif.). Others include mouse COX-2 promoter region from −203 to +70 relative to the transcription site inserted into pTIS10L vector (Kim and Fischer, J. Biol. Chem., 1998, 273, 27686-94), human uPAR promoter region from −141 to +47 relative to transcription start site in pGL3 vector (Wang et al., Eur. J. Biochem., 2000, 267, 3248-54), and human VEGF promoter sequence from −2274 to +379 inserted into the pGL2 vector (Ding et al., J. Biol. Chem., 2006, 281, 9093-100).

Immunoblot Assay and Cytoplasmic and Nuclear Preparation

To measure endogenous level of several proteins in response to TPA induction and compound I, HEK293 cells were lysed with RIPA buffer (10 mM Tris-HCl pH 7.5, 1 mM EDTA, 0.1% sodium dodecyl sulfate, 0.1% deoxycholate, and protease inhibitor). Whole cell extracts were subjected to immunoblot analysis with the following antibodies: p65 (F-6), p50 (E-10), p52 (C-5), RelB (C-19), IκBα (C-21), PCNA (F-2) were obtained from Santa Cruz Biotechnology (Santa Cruz, Calif.). IKKα, IKKβ, IKKγ, phospho-IκBα, phospho-IKKα/β, phospho-IKKγ, pohospho-Stat3 (Tyr 705 and Ser 727), phospho-p65 (Ser536 and Ser276), phospho-p44/42, phospho-JNKs were purchased from Cell Signaling (Danvers, Mass.), and α-tubulin from Sigma (St. Louis, Mo.). Nuclear and cytoplasmic extracts were prepared with HEK293 cells by NE-PER Nuclear and Cytoplasmic Extraction Reagents (Pierce Biotechnology, Rockford, Ill.) according to the manufacturer's protocol.

Quantitative Real-Time PCR

Total RNA was isolated from HEK293 cells after pretreatment with varying compound I and/or TPA stimulation by ToTALLY RNA kit (Ambion, Austin, Tex.), and first-strand cDNA was synthesized from 1 μg of the isolated total RNA using the SuperScript III First-Strand Synthesis System (Invitrogen, Carlsbad, Calif.) with random hexamers, oligonucleotide primers. cDNA was purified by QIAquick PCR purification kit (Qiagen, Valencia, Calif.) according to the manufacturer's manual. Real-time PCR was performed with iQ SYBR Green Supermix (Bio-Rad, Hercules, Calif.) by iQ5 Multicolor RT-PCR detection system (Bio-Rad, Hercules, Calif.). Primers for endogenous human IL-6 were designed by Primer 3 program (http://frodo.wi.mit.edu/). Human glyceraldehyde-3-phosphate dehydrogenase (hGAPDH) was used as a control. The sequences for RT-PCR are as follows:

```
IL-6
F: 5'-TACCCCCAGGAGAAGATTCC-3',      (SEQ ID NO: 1)
R: 5'-TTTTCTGCCAGTGCCTCTTT-3'       (SEQ ID NO: 2)
and hGAPDH
F: 5'-TGCACCACCACCTGCTTAGC-3',      (SEQ ID NO: 3)
R: 5'-GGCATGGACTGTGGTCATGAG-3'.     (SEQ ID NO: 4)
```

Electrophoretic Mobility Shift Assay (EMSA)

EMSA was performed with the nuclear fraction of HEK293 cell using LightShift Chemiluminescent EMSA Kit (Pierce Biotechnology, Rockford, Ill.) according to the manufacture's instruction. Oligonucleotides for NFκB, NF-1, and AP-1 were labeled with biotin by Biotin 3' End DNA labeling Kit (Pierce Biotechnology, Rockford, Ill.). The quantified 15 µg of nuclear extracts were incubated for 20 mins with 1 µg/µl Poly (dI.dC), biotin end-label target nucleotides in 20 µl binding buffer DNA-protein complexes were fractionated on 6% a polyacrylamide gel and transferred to a nylon membrane. The membranes were processed to detect biotin-label DNA by cross-linking, blocking, and detection incubations. Results were obtained by X-ray film exposure for 10 sec and development. The target sequences of oligonucleotides for NFκB, NF-1, and AP-1 are as follows;

```
NFκB
F: 5'-GGTTACAAGGGACTTTCCGCTG-3',    (SEQ ID NO: 5)
R: 5'-CAGCGGAAAGTCCCTTGTAACC-3',    (SEQ ID NO: 6)

NF-1
F: 5'-TTTTGGATTGAAGCCAATATGATA-3', (SEQ ID NO: 7)
R: 5'-TATCATATTGGCTTCAATCCAAAA-3', (SEQ ID NO: 8)

AP-1
F: 5'-CTAGAGGTGTCTGACTCATGCTTTA-3', (SEQ ID NO: 9)
R: 5'-AGCTTAAAGCATGAGTCAGACACCT-3'. (SEQ ID NO: 10)
```

Invasion Assay

Breast cancer cell lines, MCF-7, T47D, and MDA-MB-231 were used to measure the effect of compound I on TPA-induced invasion activity using Matrigel Invasion Chamber (BD Bioscience, San Jose, Calif.) according to the manufacturer's protocol. Matrigel-coated chambers containing an 8 µm pore size filter were fitted into a 24-well tissue culture plate. Briefly, breast cancer cells ($1 \times 10^5$ cells/ml) of each cell line were seeded into 6-well Matrigel-coated chambers with DMSO, TPA, or TPA plus compound I conditions and incubated for 24 hrs. The media wells for each plate contained only standard growth medium. After 24 hrs the non-invading cells were removed from the upper side of the chamber by cotton tipped applicators. The invaded cells on the bottom side were stained using Diff-Quik staining (Dade Behring, Deerfield, Ill.) and photographed. Three independent results were very similar.

Transformation Assay

JB6 cells (clone 41) were used to assess the inhibitory activity of compound I using CytoSelect 96-well Cell Transformation Assay (Cell Biolabs, Huissen, Netherlands) as Soft Agar Assay according to manufacturer's instructions. Cells were incubated for 10 days in 0.4% agar medium over 0.6% agar containing TPA or TPA with compound I or DMSO as a control. To measure anchorage-independent growth, agar-layers were dissolved and lysed. 10 µl of the lysed solutions of each well were mixed with CyQuant and the fluorescence read by iQ5 with a FAM filter of 485/520 nm. As an alternative analysis, cell dose curves of JB6 cells were quantified by the End point using CyQuant to indicate relative anchorage-independent colony number.

Results

Compound I Prevents Activation of NFκB

To evaluate whether the compound I biological activity can imitate TAM67 specificity, three different transcriptional promoter reporters were used, AP-1, NFκB, and SRE (Serum response element) in luciferase reporter assays (FIG. 1A: The transfected cells were pre-treated with varied concentrations of compound I or DMSO for 1 hour before 18 hours stimulation by TPA (10 ng/ml) or DMSO as vehicle. An asterisk (*) indicates a separate experiment with NFκB dependent luciferase only. Assays were performed with two independent experiments each in quadruplicate.). All three activities were induced by TPA but only induction of AP-I and NFκB were inhibited by TAM67. The SRE reporter was used as a specificity control and indicator of cell proliferation. TPA-induced SRE activity was not repressed by TAM67 when coexpressed with the SRE-Luc reporter in HEK293 cells. The same concentration (10 ng/ml, 16.2 nM) and incubation time (18 hrs) were used for TPA induction as previously used for the high throughput screen (HTS) (Ruocco et al., J. Biomol. Screen., 2007, 12, 133-9) along with 1 h pretreatment of compound I. The screening results had tested concentrations as high as 40 µM compound I with cell numbers showing 95.5+/−6.2% of DMSO control (ave+/− sd, n=3) by the XTT assay in HEK293T cells. Thus compound I showed neither cytotoxic nor cytostatic activity for HEK293 cells.

Figure 1B:
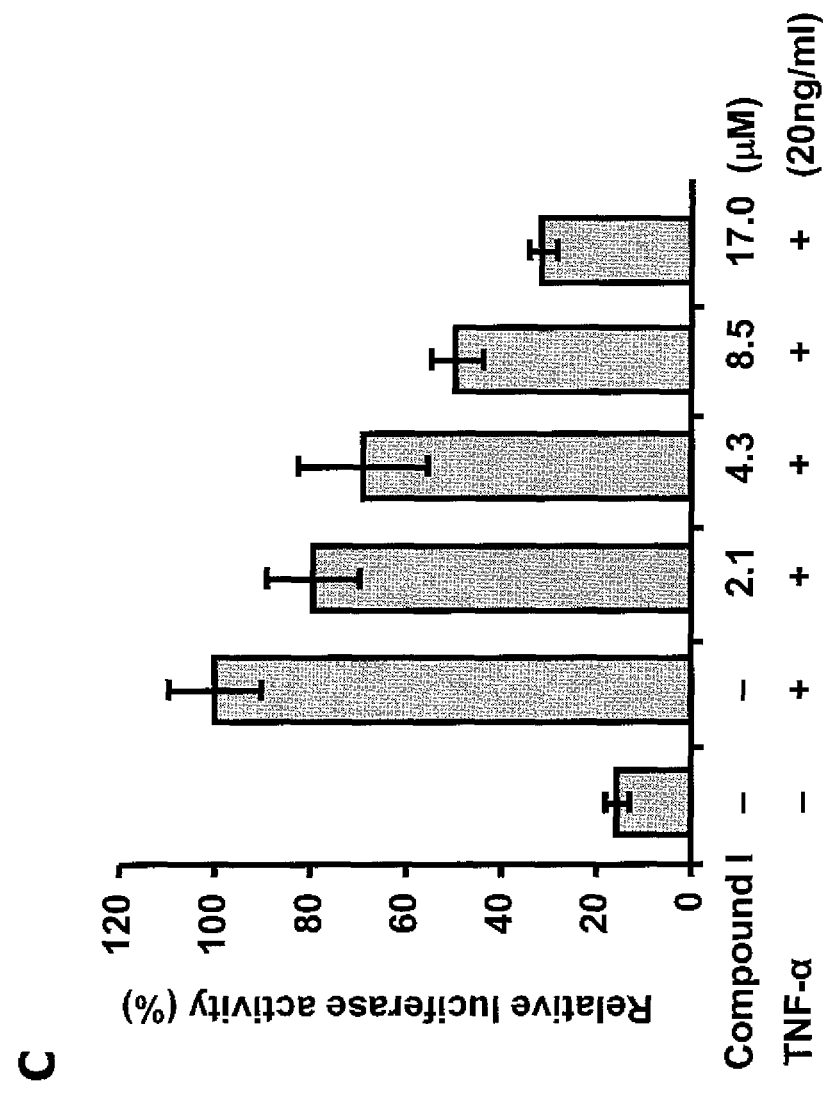
FIG. 1B is a bar graph showing relative luciferase reporter activity in the presence of increasing concentrations of compound I and in the presence or absence of TNFα.

AP-1 luciferase activity was repressed to 50% of the activity with TPA alone after pretreatment by compound I at 17.0 µM (FIG. 1A). SRE activity was also repressed but to a lesser degree than AP-1. Surprisingly, TPA-induced NFκB luciferase activity was completely blocked to the non-induced level at 17.0 µM of compound I. NFκB luciferase activity was dose-dependently inhibited by compound I at all concentrations tested. The $IC_{50}$ of compound I against TPA-induced NFκB was around 4 µM or about ¼ of the 17.0 µM $IC_{50}$ for AP-1 inhibition. The basal activity for NFκB was also inhibited, but to a lesser extent, by compound I without TPA induction (FIG. 1B: Luciferase activities with TPA or TNFα induction alone were set at 100%, and the relative activities with TPA or TNFα in the presence of compound I are shown. Assays were performed with two independent experiments each in triplicate.). In addition, compound I shows dose-dependent inhibition of NFκB induced by TNFα (FIG. 1B). These results suggest that compound I may preferentially target events needed for NFκB activation rather than other transcription factor activations. The magnitude of NFκB activity remaining in the presence of compound I suffices to support normal cell survival.

Compound I Inhibits Phosphorylation of Endogenous IκBα and IKKα/β

To characterize the activity of compound I in targeting events upstream of NFκB, endogenous levels of kinases involved in NFκB activation were examined by immunoblot analysis. The well-established upstream regulators of NFκB activation are IKKα, IKKβ, and IκBα. Stimulation of HEK293 cells with TPA resulted in induced phosphorylation of IκBα as well as of protein kinase(s) I Kappa B Kinase α and/or β. The induced phosphorylation of IκBα following TPA stimulation was almost completely blocked after pretreatment with compound I at 17.0 and 8.5 µM. A similar potency for inhibition of IKKα/β phosphorylation was seen. Moreover, the phosphorylation of IκBα was inhibited even at 1.1 µM showing dose-dependent decrease by compound I pretreatment. TPA-induced phosphorylation of IκBα was also inhibited by compound I at 6 and 12 hours. The phosphorylation of IκBα following TPA treatment showed no significant increase at less than 3 hours. In addition, compound I inhibits TNFα-induced phosphorylation of IKKα/β and IκBα at 1 hour. IKKβ from IKKα was not able to be distinguished in this analysis with antibodies which detect phosphorylated IKKα at Ser176/180 and IKKβ at Ser177/181. TPA-induced phosphorylation of IκBα is mediated primarily through IKKβ catalytic activity; thus compound I represses phosphorylation of IKKβ and in an embodiment both IKKβ and IKKα. Phosphorylation of IKKγ did not change in response to compound I pretreatment. The total protein levels of IKKα/β, IKKγ, and IκBα were not affected. Thus, upstream activation events rather than transcription factor binding to DNA are targeted by compound I when it inhibits NFκB induction.

The selectivity of compound I was evaluated by measuring phosphorylation of proteins involved in the AP-1 induction pathway. AP-1 dependent transcription can be activated by MAP Kinases JNK, ERK 1/2 (p44/42). Immunoblot assay revealed no repression of TPA-induced phosphorylation of endogenous JNK, ERK 1/2 (p42/44), or of TPA inducible phosphorylation of an unrelated transcription factor STAT3 by pretreatment with compound I at 17.0 μM and 8.5 μM. At these concentrations compound I, in contrast, completely repressed major regulators in the NFκB activation pathway. JNKs are activated by a variety of environmental stresses responsible for AP-1 activation through c-Jun phosphorylation. TPA-induced phosphorylation of INKS showed no repression by compound I pretreatment. These results indicate that compound I does not negatively regulate MAP Kinases that activate AP-1 or kinases that activate STAT3. Instead it suppresses the phosphorylation of IκBα needed for release from p65/p50 and of IKKs that activate NFκB.

Compound I In Vitro Assay

Figure 5:
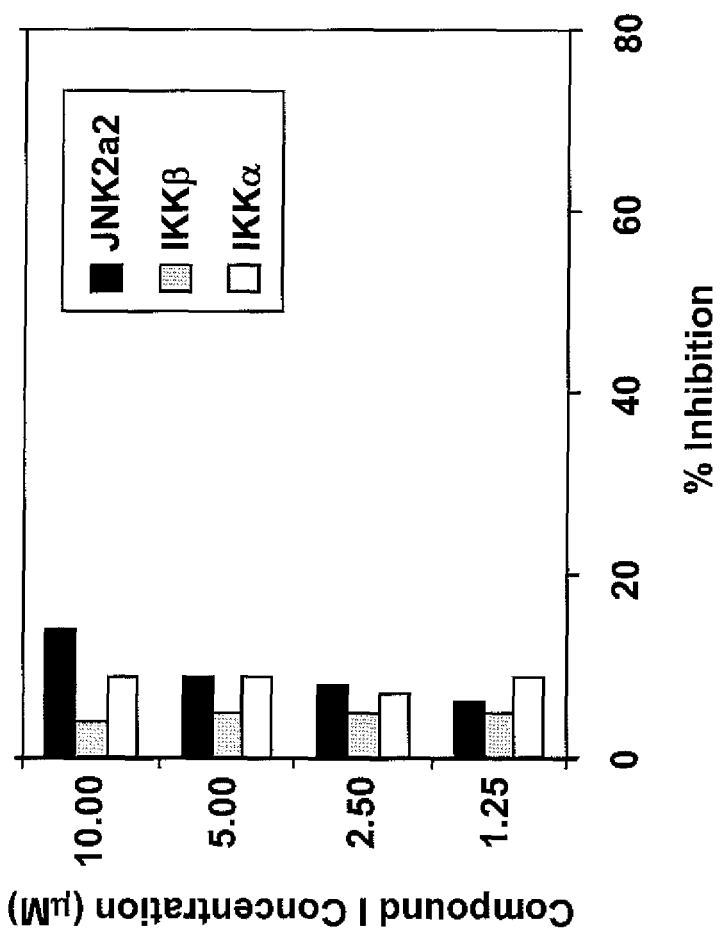
FIG. 5 is a bar graph showing percent inhibition of in vitro kinases in the presence of increasing concentrations of compound I.
Figure 7:
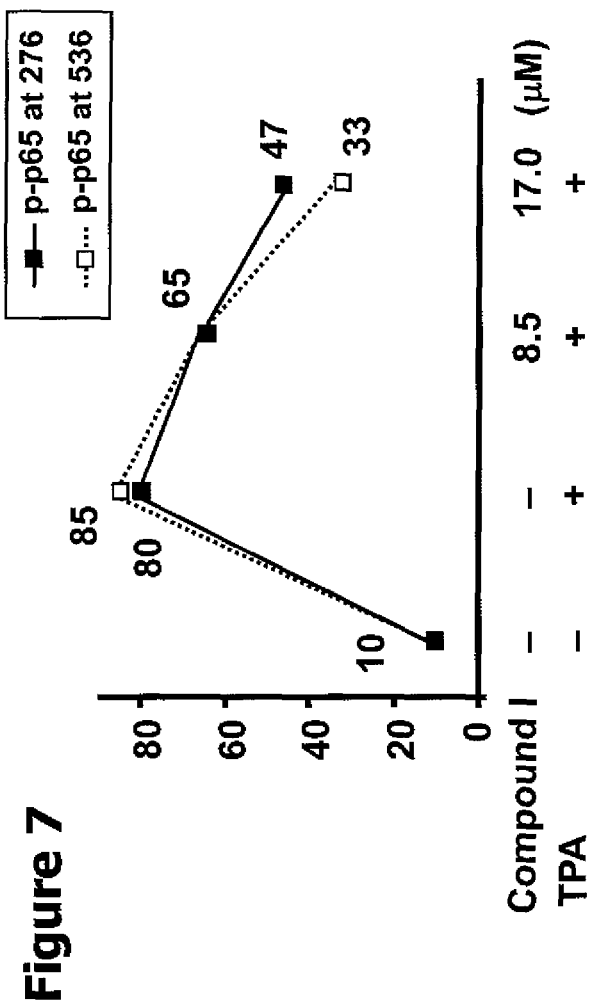
FIG. 7 shows compound I decreased the phosphorylation of p65 at Ser536 and Ser276.

In an attempt to determine whether compound I interferes with ATP binding to the catalytic site, the activity of compound I was measured with fully activated, phosphorylated IKKα or IKKβ. In an in vitro assay, the off-chip incubation mobility-shift kinase assay measuring the ability to block phosphorylation of a peptide substrate of IKKα or β, compound I does not inhibit the activity of either IKKα or β by targeting its conserved ATP binding pocket. However, whether this compound interacts outside of the ATP binding pocket of IKK as an ATP non-competitive inhibitor similar to BMS-345541 is unknown. (FIG. 5: In vitro kinase inhibition assay by the off-chip incubation mobility shift. Compound I was tested against 3 kinase targets, JNK2a2, IKKβ, and IKKα. Assay consisted of testing the compound in duplicate at concentrations of 1.25, 2.50, 5.00, and 10.00 μM. Less than 20% inhibition of binding or enzyme activity is considered inactive.). Both compound I and BMS-345541 at concentrations from 0.1 to 100 μM showed no inhibition of phosphorylation of IκBα peptide substrate catalyzed by IKKβ, incubated with ATP in an in vitro assay (Calbiochem, Gibbstown, N.J.; K-LISA™ IKKβ Inhibitor Screening Kit). BMS-345541, showed dose-dependent inhibition of NFκB-Luciferase at 1 to 8 μM without inhibition of AP-1, similar to compound I (FIGS. 1A and 6A. FIG. 6: Comparison of compound I with other IKK inhibitors for kinase and transcription factor inhibition. AP-1, NFκB, and SRE promoted luciferase inhibition by (A) BMS-345541, (B) SC-514 and (C) sulfasalazine. HEK293 cells were transfected with AP-1, NFκB, or SRE promoted luciferase reporter. The transfected cells were pre-treated with varied concentrations of BMS-345541, SC-514, sulfasalazine or DMSO for 1 hour before 18 hours stimulation by TPA (10 ng/ml) or DMSO as vehicle. Luciferase activities with TPA induction alone were set at 100% and the relative activities with TPA in the presence of compounds are shown. Reporter assays were performed with two independent experiments each in quadruplicate.) In contrast, other NFκB inhibitors ATP competitive inhibitor SC-514 and sulfasalazine showed similar or greater potency for inhibiting AP-1 and no sparing of SRE in the luciferase assay (FIGS. 6B and 6C).

Compound I Inhibits TPA-Induced Nuclear Accumulation of NFκB p65/p50 by a Mechanism Involving Inhibition of IKKβ

Nuclear translocation of endogenous p65/p50 and RelB/p52 heterodimers were monitored The activation of heterodimers p65/p50 and RelB/p52 occurs by distinct pathways dependent on IKKβ or IKKα catalytic activity. Repression of IKKβ would be expected to influence nuclear translocation of p65/p50 while repression of IKKα would influence processing of p100 to p52. Nuclear translocation of p65 (also known as RelA) and RelB were induced by TPA and translocation in both cases were remarkably repressed by pretreatment with compound I. Translocation of p65 on the canonical pathway depends on phosphorylation of IκBα by IKKβ. However translocation of RelB is only dependent on IKKα for processing of its dimer partner p52 from p100. This processing depends on phosphorylation of p100 by IKKα. The processing of p100 to nuclear p52 was not inhibited by compound I but was proportional to expression levels of p100. Compound I inhibited expression of p100 by an unknown mechanism. Thus because compound I does not inhibit the processing of p100 to p52, it appears not to inhibit IKKα. Instead compound I inhibits IKKβ.

Compound I Inhibits DNA Binding of NFκB

Figure 2A:
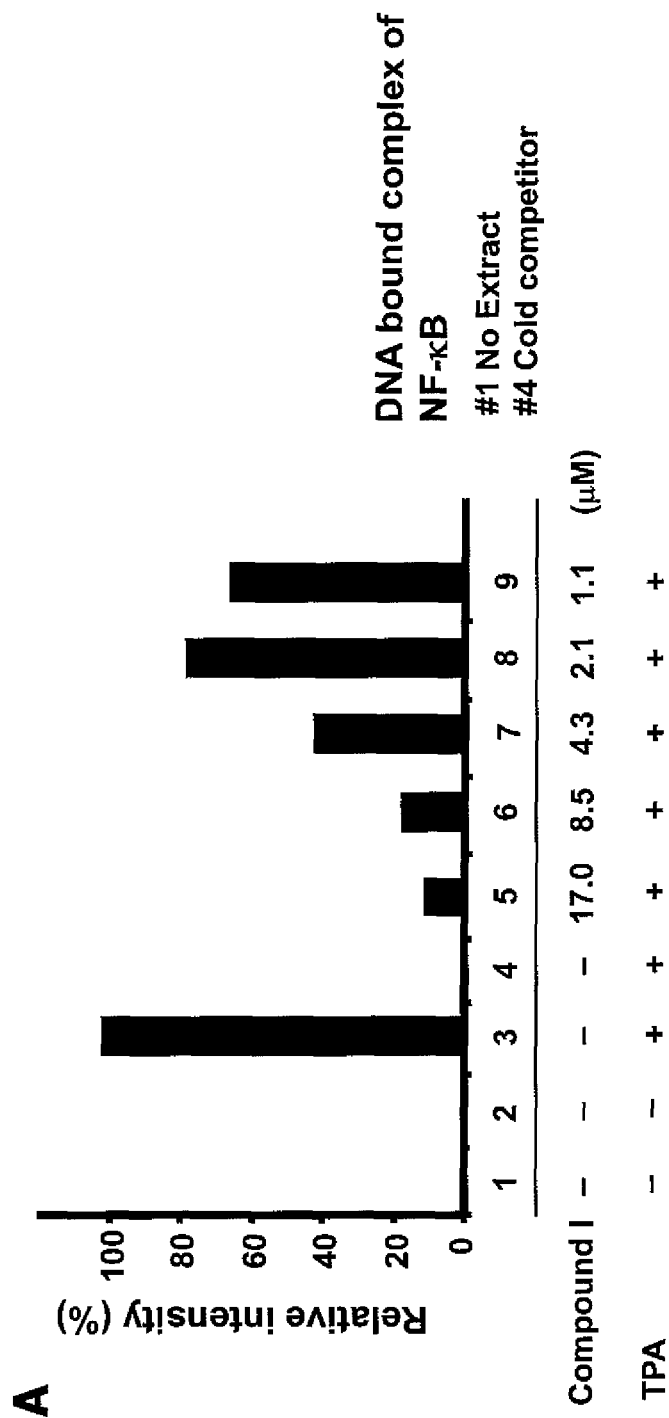
FIG. 2A is a bar graph showing densitometry readings of a gel-shift assay, showing compound I inhibits DNA binding of NFκB.
Figure 2B:
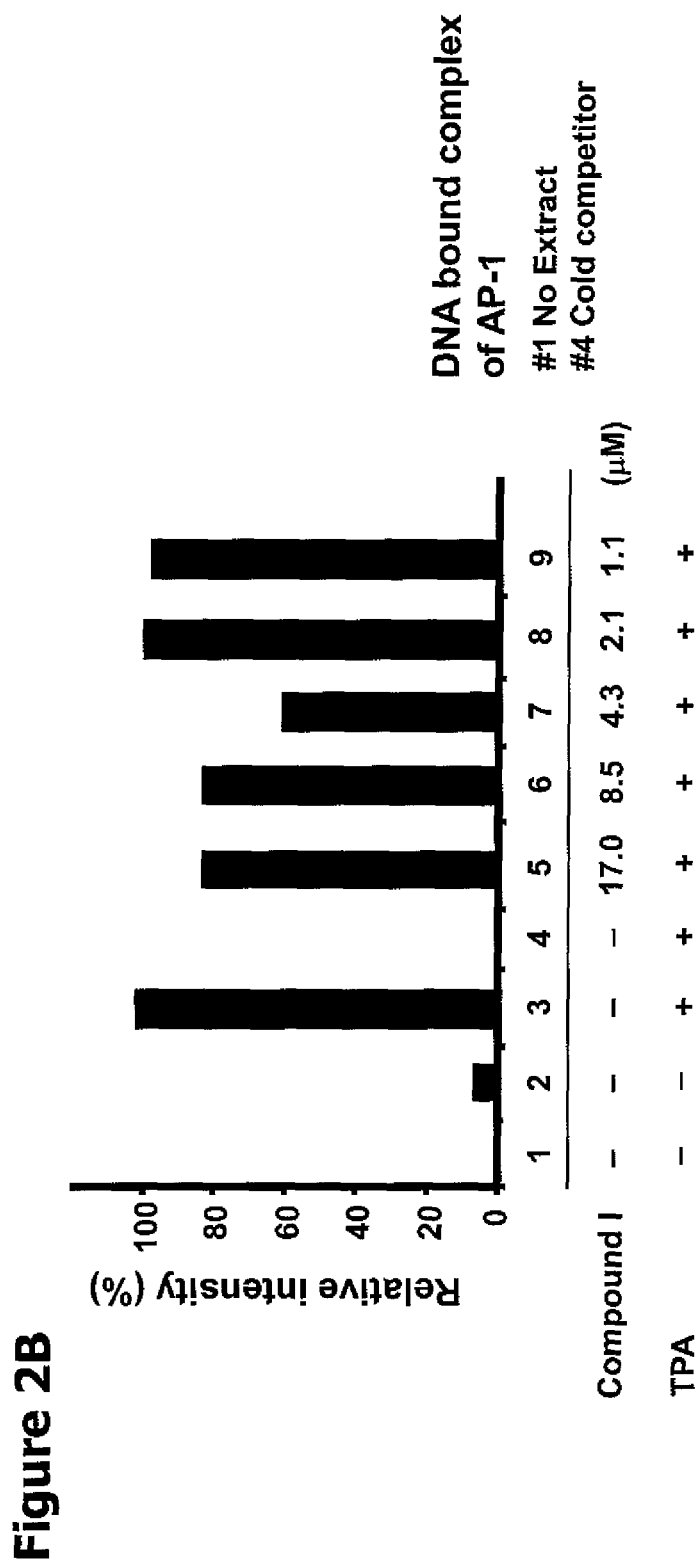
FIG. 2B is another bar graph showing densitometry readings of a gel-shift assay, showing the lack of compound I effect on AP-1 and NF-1 binding.

To determine whether the effect of compound I on nuclear translocation of NFκB leads to inhibited binding of NFκB proteins to DNA, EMSA in HEK293 cells was performed. Analysis of endogenous NFκB DNA binding activity by EMSA was tested with a probe representing an NFκB-dependent promoter (FIG. 2A: Inhibition of NFκB binding. EMSA analysis of basal and TPA-induced NFκB DNA-binding was performed with NFκB oligonucleotide probe on the nuclear fractions of HEK293 cells. HEK293 cells were treated with TPA (10 ng/ml) for 18 hours following pretreatment with compound I or DMSO for 1 hour. The lane 1 was mixed with no extract of nuclear fractions of HEK293 cells. Semiquantitative analysis of EMSA using densitometry of the band in each lane is shown. NFκB DNA binding activities were converted to the value of the maximal activity with TPA induction alone without compound I.) The intensity of NFκB probe and protein complex was increased by TPA stimulation (lane 3) and pretreatment of compound I at 17 μM resulted in marked loss of binding complex. TPA-induced binding complex was attenuated by pretreatment with compound I in a dose-dependent manner (lanes 5-9). This binding inhibition parallels the inhibition of luciferase reporter transactivation and inhibition of nuclear translocation of NFκB proteins. The TPA-induced binding complex disappeared when the labeled NFκB oligonucleotide was competed with an excess of unlabelled probe (90× fold). Specificity controls showed that compound I at 17 μM had little or no effect on NF-1 and AP-1 binding activity (FIG. 2B: Lack of compound I effect on AP-1 and NF-1 binding. EMSA analysis of basal and TPA-induced AP-1 (lane 1-9) and NF-1 (lane 10-12) DNA-binding was performed with AP-1 and NF-1 consensus probes. Semiquantitative analysis of EMSA is shown using densitometry of the band in each lane.) Taken together, these results show that compound I inhibits DNA binding as a consequence of interference with nuclear localization of NFκB proteins, a process that is regulated by IKK activity.

Figure 3A:
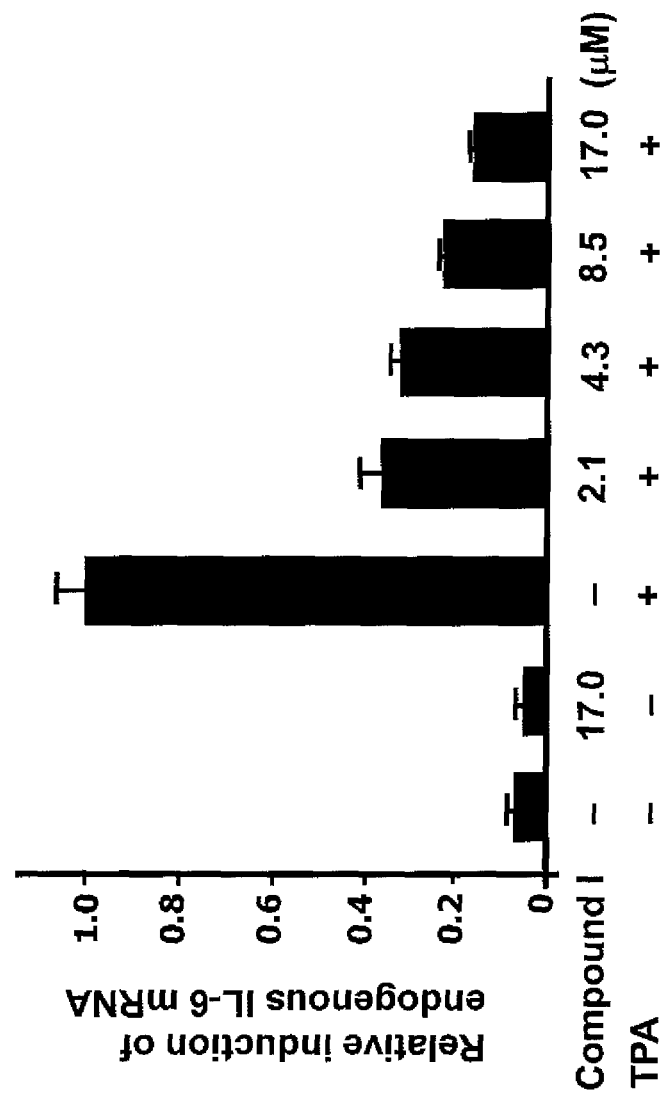
FIG. 3A is a bar graph showing relative endogenous IL-6 mRNA induction in the presence of increasing concentrations of compound I and in the presence or absence of TPA (12-O-tetradecanoylphorbol-13-acetate).
Figure 3B:
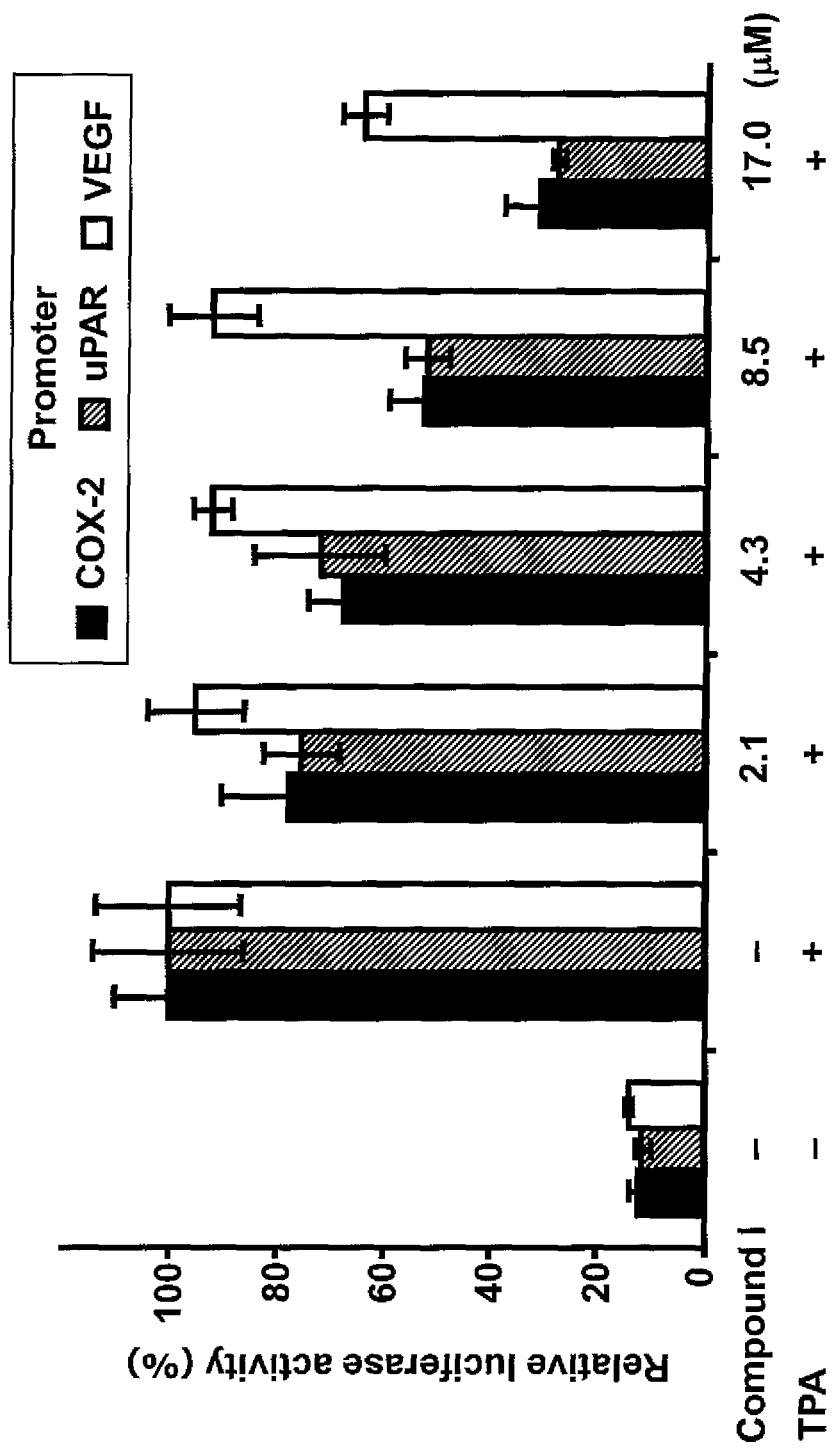
FIG. 3B is a bar graph that shows relative luciferase reporter activity of COX-2, uPAR, and VEGF promoters in the presence of increasing concentrations of compound I and in the presence or absence of TPA.

TPA-Induced Transcriptional Targets of NFκB Were Repressed by Compound I Pretreatment Inhibition of NFκB transactivation would be expected to result in suppressed expression of genes whose transcription depends on NFκB. Quantitative RT-PCR was used to measure endogenous levels of IL-6 mRNA, transcribed from a gene whose transcription depends on NFκB but not AP-1. While TPA induction increased the IL-6 mRNA by more than 10 fold, pretreatment with compound I prevented more than half of the induction at concentrations as low as 2.1 µM (FIG. 3A: IL-6 mRNA expression. Detection by quantitative RT-PCR showed TPA induced IL-6 mRNA was repressed by compound I pretreatment. Total RNA was isolated and analyzed from 18 hours TPA-treated HEK293 cells pretreated with compound I or DMSO for 1 hour. Human IL-6 mRNA was normalized by GAPDH.) The effect of compound I on several well-known transcriptional targets of NFκB, also regulatable by AP-1, was examined using luciferase reporter assays in HEK293 cells. Plasmids expressing luciferase reporters were driven by promoters for COX-2, uPAR (urokinase-type plasminogen activator receptor), or VEGF. COX-2 and uPAR luciferase activities after treatments with compound I showed similar dose-dependent inhibition (FIG. 3B: Luciferase reporter assays of NFκB targets. Promoter directed luciferase reporters for COX-2, uPAR, and VEGF were transiently transfected into HEK293 cells separately. The cells were pretreated with compound I followed by exposure to TPA (10 ng/ml) or DMSO for 18 hours. The luciferase activity attained by TPA induction only was set at 100% and used to compare the activity in the presence of compound I. Assays were performed in triplicate.). In contrast, compound I did not significantly affect the luciferase activity when driven by VEGF promoter. One NF-IL6 and two AP-1-like sequences are located in the promoter region of COX-2. uPAR promoter region contains one NFκB-like sequence and two AP-1 binding sites, and VEGF promoter region has multiple binding sites for AP-1, HIF-1α, and NFκB-like. These mixed promoter regions of AP-1 and NFκB in the COX-2 and uPAR are known to be important sequences for their expression. However, VEGF has not shown direct dependency on an NFκB consensus sequence in the promoter region of mouse macrophages, whereas several AP-1 and HIF-1α sites are required. Deletion of putative NFκB binding sites from the VEGF promoter reporter shows no effect, suggesting that NFκB is not directly involved in VEGF transcription. The significant differential in sensitivity to compound between VEGF versus COX-2 and uPAR as shown in FIG. 3B, might be explained by the relative importance of NFκB binding sites compared to AP-1 sites in the promoter region. These results establish that genes known to be dependent on NFκB are transcriptionally inhibited by compound I.

Compound I Suppresses TPA-Induced Transformation and Invasion

Figure 4:
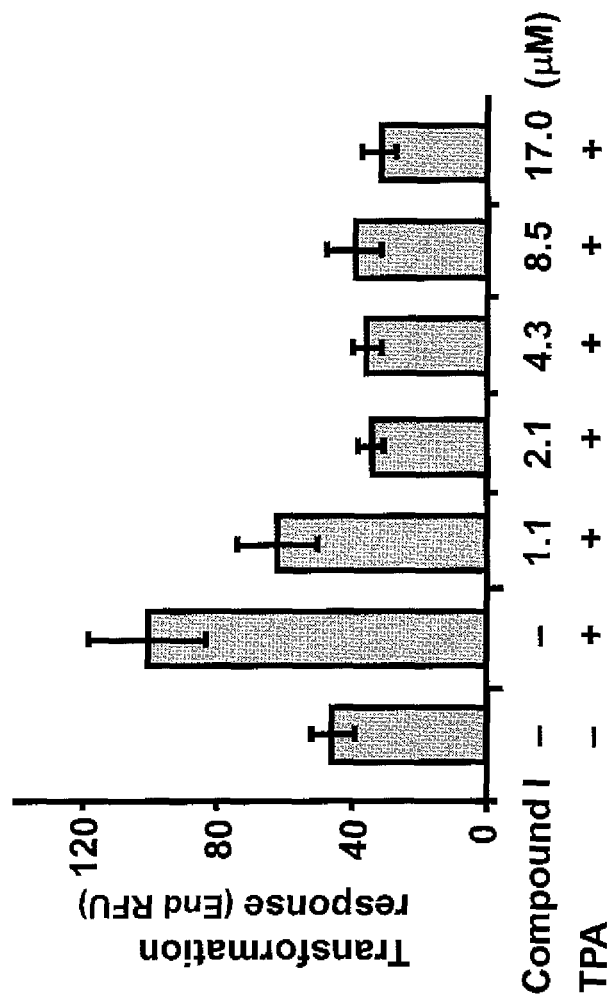
FIG. 4 is a bar graph that shows JB6 cell transformation response in the presence of increasing concentrations of compound I and in the presence or absence of TPA.

In order to evaluate the potential therapeutic activity of the compound, tests for the biological activity of compound I were performed. The compound is non-toxic to MCF-7, T47D, and MDA-MB-231 breast cancer cells as estimated by XTT assay at 10 µM. To determine the effects of compound I on invasion by breast cancer cell lines, a matrigel invasion assay was used. The levels of phosphorylated IκBα were confirmed in TPA treated ER-positive (MCF-7 and T47D) and ER-negative (MDA-MB-231) breast cancer cell lines and compared the levels to those after pretreatment with compound I. Although induced levels of phosphorylated IκBα varied with the cell line, IκBα phosphorylation was eliminated by compound I treatment in all three breast cancer cell lines. Compound I also produced no effect on the estrogen receptor activity in the ER-positive breast cancer cells using ERE promoter luciferase reporter assay. Invasion capacity of breast cancer cells was increased by TPA stimulation compared to DMSO treated vehicle control. However, compound I completely inhibited the TPA-increased invasion in the three breast cancer cell lines as well as basal invasive activity in MBA-MB-231 cells. In another assay, to assess the inhibitory effect of compound I on TPA-induced transformation, soft agar assays were performed in mouse JB6 cells using the Cytoselect 96-well cell transformation assay. Following anchorage-independent colony induction in TPA-treated cells without or with compound I, colonies were lysed and measured with CyQuant GR Dye to detect DNA by fluorescence plate reader as a measure of colony count. Total transformed colony numbers were calculated from RFU and cell dose curve of JB6 cells. End RFU measuring DNA concentration is proportional to the number and size of anchorage independent JB6 colonies (FIG. 4: Anchorage-independent transformation response. JB6 cells were suspended in soft agar and incubated with medium containing TPA (10 ng/ml) with compound I or DMSO for 10 days.) Transformation response to TPA was repressed to below vehicle control level by compound I treatment at 17.0 µM to 2.1 µM. Compound I even decreased transformation response at 1.1 µM. This result is consistent with the immunoblot analysis showing expression levels of phosphorylated IκBα inhibited by compound I treatment at 1.1 µM. Thus, these results demonstrate that compound I, when it blocks phosphorylation of IκBα completely blocks the TPA-induced invasion in breast cancer cells and the transformation response in JB6 cells.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A pharmaceutical composition comprising (i) a compound of the formula

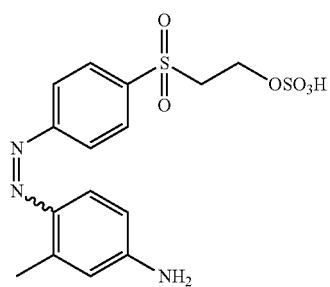

or a pharmaceutically acceptable salt, prodrug, hydrate, or solvate thereof, and (ii) a pharmaceutically acceptable carrier.

2. The pharmaceutical composition of claim 1, wherein the composition further comprises at least one additional compound that inhibits an NFκB pathway.

3. The pharmaceutical composition of claim 2, wherein the at least one additional compound is ibuprofen, sulindac, curcumin, aspirin, sulfasalazine, SC-514, BMS-345541, MLN120B or PS-1145.

4. The pharmaceutical composition of claim 1, wherein the compound, pharmaceutically acceptable salt, prodrug, hydrate, or solvate is in the Z (cis) configuration.

5. The pharmaceutical composition of claim 1, wherein the compound, pharmaceutically acceptable salt, prodrug, hydrate, or solvate is in the E (trans) configuration.

6. A method of treating a condition associated with increased expression and/or activity of an NFκB pathway, the method comprising administering to an individual in need thereof an effective amount of a compound of the formula

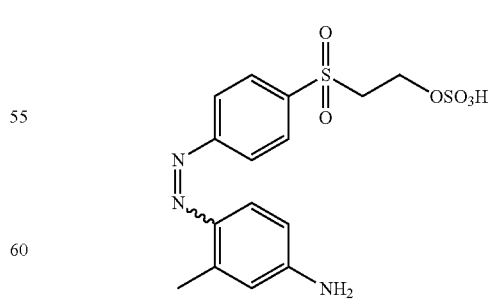

or a pharmaceutically acceptable salt, prodrug, hydrate, or solvate thereof.

7. The method of claim 6, wherein the condition is cancer tumorigenesis or tumor progression.

8. The method of claim 7, wherein the cancer is in an epithelial tissue.

9. The method of claim 7, wherein the cancer is breast cancer.

10. The method of claim 7, wherein the cancer is leukemia.

11. The method of claim 6, wherein the condition is inflammation.

12. The method of claim 6, wherein the condition is colitis, diabetes, prostatitis, pancreatitis, atherosclerosis, inflammatory bowel disease, rheumatoid arthritis, gastritis, or asthma.

13. The method of claim 6, wherein the compound, pharmaceutically acceptable salt, ester, hydrate, or solvate is coadministered with at least one additional compound that inhibits an NFκB pathway.

14. The method of claim 13, wherein the at least one additional compound is coadministered simultaneously with the compound, pharmaceutically acceptable salt, ester, hydrate, or solvate.

15. The method of claim 13, wherein the at least one additional compound is coadministered sequentially before or after administration of the compound, pharmaceutically acceptable salt, ester, hydrate, or solvate.

16. The method of claim 13, wherein the at least one additional compound is ibuprofen, sulindac, curcumin, aspirin, sulfasalazine, SC-514, BMS-345541, MLN120B or PS-1145.

17. The method of claim 6, wherein the compound or pharmaceutically acceptable salt, prodrug, hydrate, or solvate inhibits the expression or activity of IKKα, IKKβ, NFκB1, or NFκB2.

18. A method of diagnosing a condition in an individual, wherein said condition is suspected to be associated with an increased expression and/or activity of an NFκB pathway, the method comprising (i) contacting a biopsy from the individual with a compound of the formula

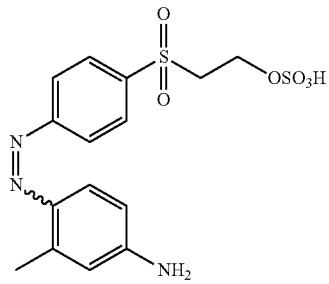

or a pharmaceutically acceptable salt, prodrug, hydrate, or solvate thereof, (ii) measuring the expression and/or activity of an NFκB pathway in the biopsy, and (iii) comparing the expression and/or activity measured in (ii) with that of a biopsy exhibiting the condition not in the presence of the compound, pharmaceutically acceptable salt, prodrug, hydrate, or solvate thereof, whereby a decrease in the expression and/or activity in the contacted biopsy indicates that the individual has a condition associated with increased expression and/or activity of an NFκB pathway.

19. The method of claim 18, wherein the biopsy is of breast tissue or cells.

20. The method of claim 18, wherein the biopsy is of blood cells.

* * * * *

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Synthetic DNA Primer

<400> SEQUENCE: 1
tacccccagg agaagattcc                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic DNA Primer

<400> SEQUENCE: 2
ttttctgcca gtgcctcttt                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic DNA Primer

<400> SEQUENCE: 3
tgcaccacca cctgcttagc                                              20

<210> SEQ ID NO 4
<211> LENGTH: 21
<212> TYPE: DNA
<213> ORGANISM: Artificial Sequence
<220> FEATURE:
<223> OTHER INFORMATION: Synthetic DNA Primer

<400> SEQUENCE: 4
ggcatggact gtggtcatga g                                            21

<210> SEQ ID NO 5
<211> LENGTH: 22
<212> TYPE: DNA
<213> ORGANISM: Artificial Sequence
<220> FEATURE:
<223> OTHER INFORMATION: Synthetic DNA Oligonucleotide

<400> SEQUENCE: 5
ggttacaagg gactttccgc tg                                           22

<210> SEQ ID NO 6
<211> LENGTH: 22
<212> TYPE: DNA
<213> ORGANISM: Artificial Sequence
<220> FEATURE:
<223> OTHER INFORMATION: Synthetic DNA Oligonucleotide

<400> SEQUENCE: 6
cagcggaaag tcccttgtaa cc                                           22

<210> SEQ ID NO 7
<211> LENGTH: 24
<212> TYPE: DNA

```
<213> ORGANISM: Artificial Sequence
<220> FEATURE:
<223> OTHER INFORMATION: Synthetic DNA Oligonucleotide

<400> SEQUENCE: 7
ttttggattg aagccaatat gata                                    24

<210> SEQ ID NO 8
<211> LENGTH: 24
<212> TYPE: DNA
<213> ORGANISM: Artificial Sequence
<220> FEATURE:
<223> OTHER INFORMATION: Synthetic DNA Oligonucleotide

<400> SEQUENCE: 8
tatcatattg gcttcaatcc aaaa                                    24

<210> SEQ ID NO 9
<211> LENGTH: 25
<212> TYPE: DNA
<213> ORGANISM: Artificial Sequence
<220> FEATURE:
<223> OTHER INFORMATION: Synthetic DNA Oligonucleotide

<400> SEQUENCE: 9
ctagaggtgt ctgactcatg cttta                                   25

<210> SEQ ID NO 10
<211> LENGTH: 25
<212> TYPE: DNA
<213> ORGANISM: Artificial Sequence
<220> FEATURE:
<223> OTHER INFORMATION: Synthetic DNA Oligonucleotide

<400> SEQUENCE: 10
agcttaaagc atgagtcaga cacct                                   25
```